United States Patent [19]

Fukuda

[11] Patent Number: 5,369,002

[45] Date of Patent: Nov. 29, 1994

[54] METHOD OF DETECTING INJURED NUCLEAR DNA

[75] Inventor: Masaru Fukuda, Fukui, Japan

[73] Assignee: Maruzen Petrochemical Co., Ltd., Tokyo, Japan

[21] Appl. No.: 40,972

[22] Filed: Mar. 31, 1993

[30] Foreign Application Priority Data

Apr. 1, 1992 [JP] Japan .................................. 4-105221

[51] Int. Cl.[5] .............................................. C12Q 1/68
[52] U.S. Cl. ........................................ 435/6; 435/7.23; 435/7.4; 435/7.5; 435/7.9; 435/960; 435/962; 436/518; 436/548
[58] Field of Search ................... 435/6, 7.23, 7.4, 7.5, 435/7.9, 960, 962, 968; 436/518, 548, 513

[56] References Cited

FOREIGN PATENT DOCUMENTS 0057553 8/1982 European Pat. Off. .
62-8053 1/1987 Japan ............................ G01N 33/50

OTHER PUBLICATIONS

Van Loon et al., Immunochemical Detection of DNA Damage Induction and Repair at Different Cellular Stages of Spermatogenesis of the Hamoxer after in Vitro or in Vivo Exposure to Ionizing Radiation. Exptl. Cell Res. 193: 303–309, 1991.

Mezzanotte et al, *Cytogenetics and Cell Genetics,* 50(1):54–58 (1989).

Dinjens et al, *Histochemistry,* 98(3):199–205 (1992).

English Language Abstract for JP-A-62-8053.

*Primary Examiner*—Esther M. Kepplinger
*Assistant Examiner*—Donna C. Wortman
*Attorney, Agent, or Firm*—Sughrue, Mion, Zinn, Macpeak & Seas

[57] ABSTRACT

An easy method for detecting injured cell nuclear DNA is provided which does not suffer from "pseudo-positive" staining. The method comprises the steps of subjecting a pathological tissue specimen to acid-hydrolysis to selectively hydrolyze any injured DNA thereby to form single-stranded DNA, then treating the specimen with an anti-single-stranded DNA antibody, and subjecting the specimen to morphological inspection to find the presence of the binding of the antibody to the single-stranded DNA. The binding may be discriminated by a labelling marker on the antibody. Alternatively, a labelled secondary antibody which binds to the anti-ssDNA antibody may be used.

13 Claims, 3 Drawing Sheets

METHOD OF DETECTING INJURED NUCLEAR DNA

BACKGROUND OF THE INVENTION

1. Field of the Invention

The present invention relates to a method of detecting injured cell nuclear DNA. More in detail, it is directed to the method for the detection of qualitative change of the cell nuclear DNA induced by carcinogenesis or like, and may be utilized in screening of cancer or malignant cells and for pathological diagnosis of cancer, or in a test for confirming the presence or absence of chemical carcinogenic substance.

2. Description of Prior Art;

It has been well known in the art that the cell nuclear DNA is quantitatively changed by aging or carcinogenesis, and the method for the detection thereof has already been established. However, it has been known that the cell nuclear DNA suffers the following qualitative alterations before it suffers the clear change as aforementioned. For example, known DNA alterations include:

1) Minute distortion due to alkylation of DNA base;
2) Small distortion due to hydration or break off of DNA base;
3) Large distortion induced by the interaction of a chemical substance (acting as an adduct) which has a large molecular weight to be interposed inbetween the DNA base linkage while forming a covalent bond;
4) Breakdown at the straight chain portion of DNA induced by the formation of a double-stranded DNA dimer, which is formed by coupling of two bases, or the formation of a cross-linking bond between the double-stranded DNAs or a cross-linking bond between the DNA chain and a protein; and
5) Injury of the nuclear DNA, e.g. shearing of double strands.

Development of a method of detecting such injured cell nuclear DNA is earnestly demanded, as a natural demand, and various methods have been proposed. For example, there is known a method in which the auto-repair of injured DNA, which is the characteristic for repairing injured DNA in the cell nucleus, is utilized so that nucleotide labelled with a radioactive isotope is incorporated in the repaired DNA followed by detection of the nucleotide labelled with the radioactive isotope. However, this known method has some problems that a special equipment is needed due to the use of radioactive isotopes, and that the capacity of the equipment is limited.

The method precedingly proposed by the inventor in Unexamined Japanese Patent Publication No. 8053/1987 is a method in which a single-stranded DNA is prepared from a cell suspension sample or from a fixed tissue specimen on a glass slide by proper method, and then the stainability by the use of acridine orange is examined. This method is based on the finding that injured nuclear DNA is selectively hydrolyzed by treating the same with an acid under an appropriate condition to produce single-stranded DNA. Based on this finding, the proposed method utilizes differential fluorescent staining of cancerous cell by using acridine orange. When acridine orange binds to double-stranded DNA as a manner of intercalation, it emits orthochromatic green fluorescence. When acridine orange binds to single-stranded DNA by stacking, it emits red-shifted metachromatic fluorescence due to dye aggregation.

In general, the tissue samples prepared for the pathological diagnosis are samples or specimens fixed with formalin. DNA strand might be injured occasionally leading to trivial injury thereof during the step of fixation with formalin to form DNA strands which are resulted by partial unlinking. In the method proposed by Unexamined Japanese Patent Publication No. 8053/1987, acridine orange may stack in to the single-stranded portions of DNA which have been formed partially with such trivial distortion. As a result, there arises another problem that the specimen fixed with formalin prepared for the pathological diagnosis suffers "pseudo-positive" stainability and thus a smear specimen prepared by grinding a fresh tissue must be used as the sample to be inspected.

It is preferable to digest the sample with RNase prior to acid-hydrolysis of DNA to remove RNA. By the addition of this digestion step, it becomes possible to prevent occurrence of "pseudo-positive" stainability resulted from the conjugation of RNA with the anti-single-stranded DNA antibody.

OBJECTS AND SUMMARY OF THE INVENTION

The present invention has been accomplished under the circumstances as described above, and the object thereof is to provide a method of detecting injury of the cell nuclear DNA from which single-stranded DNA is easily detected without the need of special equipment easily by the use of an ordinary pathological specimen, which has been prepared by fixing with formalin for the purpose of histochemical staining in the normal pathological test, without the fear of occurrence of "pseudo-positive" stainability.

The object of the invention as aforementioned has been attained by the provision of a method of detecting injured cell nuclear DNA, comprising the steps of treating a pathological tissue specimen with an acid to selectively hydrolyze any injured DNA in said pathological tissue specimen to form single-stranded DNA, then treating said pathological tissue specimen with anti-single-stranded DNA antibody, and subjecting said pathological tissue specimen to morphological inspection to find the presence of said antibody conjugated with said single-stranded DNA.

More in detail, the present invention resides in an immuno-chemical detection of the single-stranded DNA while using an anti-single-stranded DNA antibody, which is developed while apprehending the fact that the kinetics of hydrolysis of DNA is delicately affected by the form of the DNA mode thereof (e.g. its interrelation with the nuclear proteins, the presence of injured DNA molecules, etc.) so that the behaviour of normal nuclear DNA during hydrolysis differs from that of injured nuclear DNA when nuclear DNA is hydrolyzed with an acid, leading to a possibility that injured nuclear DNA can be selectively hydrolyzed to form single strands from the double strand of DNA under an appropriately selected condition, whereby the thus single-stranded nuclear DNA can be detected immuno-chemically with the use of an anti-single-stranded DNA antibody.

Such an anti-single-stranded DNA antibody tends to conjugate only with the thus separated single-stranded DNA having a size large enough to be recognized as an antigen without coupling with a partial single-stranded portion (which has a size of not-acting as an antigenic determinant in the molecular scale) due to trivial injury by the fixation with formalin or due to other causes. Accordingly, there occurs no "pseudo-positive" stainability due to the presence of any injury artificially produced by the operation in the step of preparing the tissue section or specimen.

It is preferable that the tissue section or specimen is additionally subjected to counter nuclear staining, while using, for example, hematoxylin or kernechtrot for an easier inspection in the subsequent morphological examination.

DESCRIPTION OF THE APPENDED DRAWINGS:

The above and other objects and advantages of the invention will become apparent from the following description thereof while referring to the appended drawings, in which:

FIG. 1 is a microscopic picture for the inspection of a uterine cervical tissue (intra-epithelial cancer in tunica mucosa of cervix uteri) processed through the method of the invention. In the upper half of the figure, there is shown that the cell nuclei are densely stained to reveal the presence of the tumor tissue which is bound positive to the anti-single-stranded DNA antibody. The portion in the lower half of the figure is shown to be bound negative to the anti-single-stranded DNA antibody to reveal that it is occupied by normal submucosa stromal tissue.

FIG. 2 is a microscopic picture for the inspection of a normal uterine cervical tissue which has been processed through a process similar to the method of the invention. The field of vision thereof is coincident with that of FIG. 1. No staining by the anti-single-stranded DNA antibody is recognizable in the normal epithelial mucosa which spreads over the center of the figure. The submucosal stromal tissue is also negatively stained.

FIG. 3 is a microscopic picture for the inspection of a cancerous tissue of the prostate processed similarly. The portion densely occupied by the cells having relatively large nuclei and dyed to liver-brownish color, the portion being present around and below the hollow cavity, contains cancer tissues.

FIG. 4 is a microscopic picture of the cancerous tissue in the large intestine, which has been subjected to antibody treatment with mouse monoclonal anti-ssDNA antibody and then stained by kernechtrot staining followed by cobalt-DAB coloring according to the method of the invention (Example 3). All cancer cell nuclei in the tissue forming the tubulus were positive to cobalt-DAB coloring to show that the colored portions are occupied by cancerous tissues.

FIG. 5 is a microscopic photograph of the normal tissue of the tunica mucosa of the same patient, which has been subjected to the same processing procedure as described in the preceding description of FIG. 4.

DETAILED DESCRIPTION OF THE EMBODIMENTS

Figure 1:
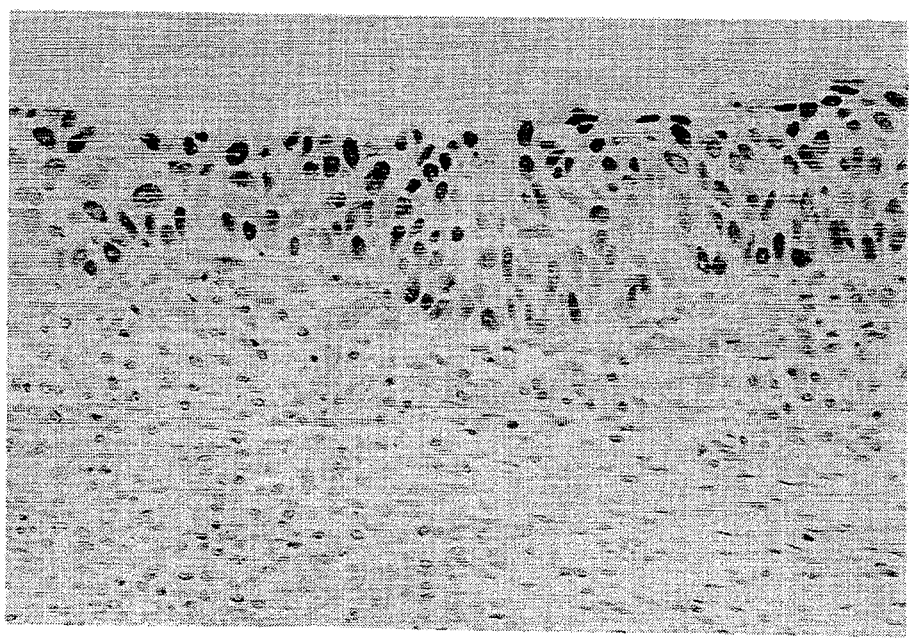

In the present invention, a pathological tissue specimen, which is provided in the form of normal paraffin-embedded section fixed with formalin, can be used as the sample to be inspected. However, the specimen usable in the invention is not limited thereto, the samples to be used as the test sample in the invention include smear of tissue cell suspensions on which cells are coated on preparations by any proper means.

The sample is (in case where the sample is an ordinary pathological tissue specimen in the form of a paraffin-embedded section prepared from the formalin-fixed specimen, after it is rinsed with a phosphate buffer solution) hydrolyzed with an acid under a gentle condition such that only the injured DNA is selectively hydrolyzed.

Such a condition for hydrolysis may be easily determined by the ordinary skill in the art through a preliminary experiment. In general, injured cell nuclear DNA can be predominantly hydrolyzed by hydrolyzing the same at a temperature of not higher than 40° C. for 5 to 120 minutes, preferably at 20° to 35° C. for about 15 to 30 minutes, while using an acid, such as hydrochloric acid, sulfuric acid, phosphoric acid, nitric acid or perchloric acid (for example, when hydrochloric acid is used, it is pertinent to use 1N to 5N hydrochloric acid) in a diluted condition.

It is preferable to subject the sample to hydrolysis while using a 2N hydrochloric acid at 30° C. for 20 minutes when the sample used is a paraffin-embedded section; whereas the sample is subjected to hydrolysis preferably using 2N hydrochloric acid at 30° C. for 8.5 minutes when the sample used is a smear of tissue cell suspension.

By treating the thus produced single-stranded DNA with an anti-single-stranded DNA antibody, followed by inspection through a microscope to ascertain the presence of any binding of antibody in the inspected tissue sample or to check the distribution of the bindings of the antibody, cancerous or malignant cells can be detected. By using an antibody labelled with a colored dye such as Rhodamine, Texas red or like, or labelled with a fluorescent dye such as FITC or like, it is made easier to conduct the morphological observation.

Alternatively, an antibody labelled with an enzyme, such as peroxidase, alkali phosphatase or like, or a enzyme such as biotin may be used, followed by special dyeing while making use of the particular enzymatic reaction after the treatment with respective enzymes.

In a further alternative wherein no labelled anti-single-stranded DNA antibody is used, an immuno-histochemical staining treatment, wherein the sample is stained by treating with a labelling secondary antibody (anti-IgG antibody) after it is treated with an anti-single-stranded DNA antibody, may be effected and then the thus treated sample is observed.

The anti-single-stranded DNA antibody may be the one which does not cause any cross-linking reaction with the double-stranded DNA, and anti-sera obtained from animals which are immunized with single-stranded DNA through the ordinary process may be used. In the detection method of the invention, monoclonal antibodies may also be used. Alternatively, antibodies against deoxyribonucleotides, such as anti-cytidine antibody, may also be used.

According to the present invention, as will be seen from the foregoing, simply by the utilization of gentle hydrolysis with a dilute acid and the conjugation with a labelling anti-single-stranded DNA antibody, any injured DNA can be discriminated from double-stranded DNA without the occurrence of the problem of "pseudo-positive" stainability, even when an ordinary paraffin-embedded section fixed with formalin usually prepared for the pathological diagnosis is used as the sample, whereby detection of cancer cell becomes possible.

EXAMPLES OF THE INVENTION

Example 1

Bovine serum albumin (BSA) was dissolved in methyl alcohol to prepare a 1% (w/v) solution to which a 12N hydrochloric acid solution was added to obtain a 0.84% (v/v) solution. The suspension was allowed to stand at a cold and dark place for 3 days while stirring the same intermittently. Then, rinsing was effected by centrifugation for two time with methyl alcohol and further two times with anhydrous ether. After evaporating ether from the precipitate, the precipitate was dried on KOH in vacuum and preserved in the powdered form with KOH. The thus obtained product (methylated BSA (MBSA)) was used as a carrier for modifying the antigen.

As an antigen, calf thymus DNA was dissolved in a 0.15M NaCl solution to a concentration of 500 ug/ml, which is preserved in a boiled water (100° C.) for 10 minutes and then rapidly cooled in ice-chilled water. A 1% aqueous solution of MBSA was added to the thus obtained aqueous solution of single-stranded DNA (ssDNA) while stirring, until the final weight ratio of MBSA to ssDNA reached 1:1. The thus obtained admixture (i.e. a suspension of ssDNA-MBSA conjugate) was emulsified with the equal volume of the complete Freund's adjuvant.

To prepare an anti-serum, the emulsified single-stranded DNA (antigen) having a concentration of 0.24 mg single-stranded DNA/ml was injected to a foot pad and a femoral muscle of a rabbit for 3 weeks at a dosage of one time a week. The blood of the rabbit was taken after one week from the completion of final injection to obtain a serum which was used as an anti-ssDNA serum.

Paraffin-embedded tissue sections were prepared from the biopsy specimens fixed with formalin through the ordinary process taken from cancerous tissue at the uterine cervix and the normal tissue of the same uterine cervix. They were deparaffinized, subsequently treated with RNase A (Ribonuclease A, Type-AS, from bovine pancreas, Sigma, USA) for 30 minutes and with a 2N hydrochloric acid solution for 20 minutes, and then allowed to react with rabbit anti-ssDNA serum at 4° C. for 12 hours. After rinsing with a phosphate buffer solution (PBS), the tissue sections were allowed to react with biotinylated anti-rabbit IgG antibody (a secondary antibody) at 37° C. for an hour, followed by rinsing similarly with PBS, and then allowed to react with peroxidase-labelled streptavidin. After additional rinsing with PBS, the tissue sections were colored with DAB coloring solution (0.01% 3,3'-diaminobenzidine, 50 mM Tris-HCl (pH 7.6)), and observed through a microscope. The result is shown in FIG. 1.

Referring to FIG. 1, the cancerous portion (the upper half in the Figure) is observed to have DNA, which is single stranded by the treatment with hydrochloric acid and coupled with the anti-ssDNA rabbit IgG, a further coupling of it with the biotinylated anti-rabbit IgG antibody conjugate with avidin being also observed. This figure is a picture of the uterine cervix tissue at which dense malignant cells were observed, where only the malignant cell nuclei (at the upper half portion of the figure) were distinctively and selectively colored to liver-brown. The lower half of the figure shows the normal tissue of submucosa which is negative to the anti-single-stranded DNA anti-serum.

Figure 2:
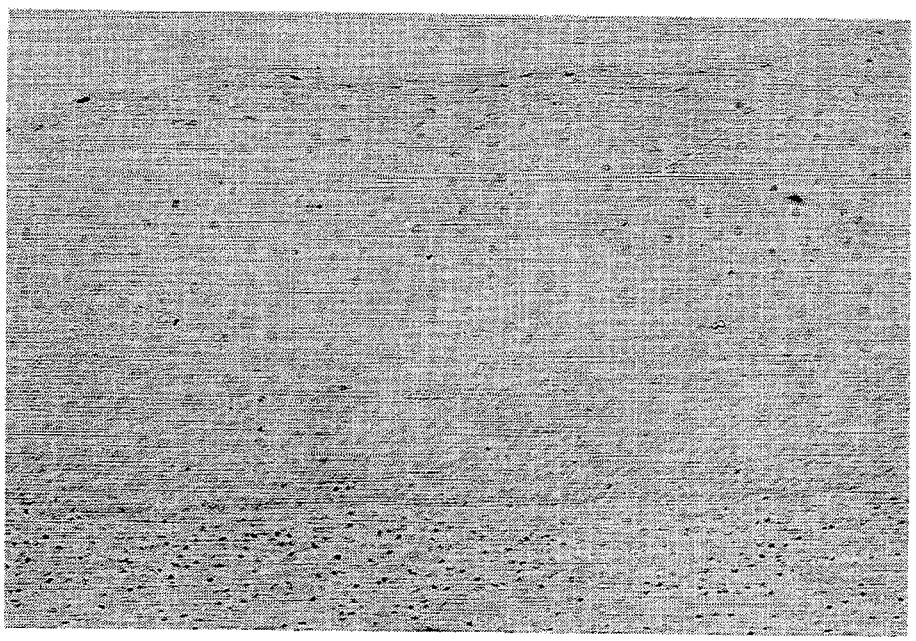

On the other hand, the normal tissue of the uterine cervix of the same patient was processed similar to the example. As shown in the inspection picture through a microscope of FIG. 2, the normal tissue had no nucleus which was stained or colored to liver-brown.

Example 2

Similar to the procedure as in Example 1, the ordinary pathological specimen taken from human prostatic carcinoma tissue was subjected to the acid-hydrolysis and immunohistochemical staining with an anti-ssDNA anti-serum. The result is shown in FIG. 3.

Figure 3:
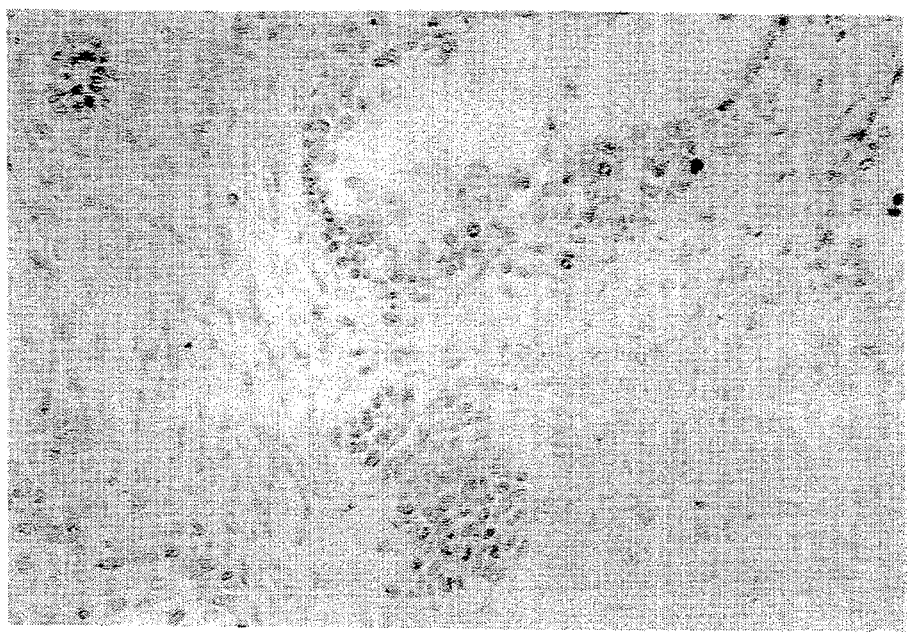

FIG. 3 shows a microscopically inspected image of the prostatic carcinoma tissue which has been processed similarly as in Example 1. A portion, in which relatively large nuclei are present and nuclei colored to liver-brown are densely present, was observed at the portion around and below the hollow cavity at the central upper half in the figure. This portion contains cells having the nuclei larger than those surrounding the same, and thus it is acknowledged that the cells which have large and liver-brown colored nuclei are cancerous.

As seen, it has been confirmed that the normal cell and the cancerous cell can be discriminated from each other by staining with the use of an anti-ssDNA antibody.

Example 3

A monoclonal anti-single-stranded DNA antibody was prepared, and the nuclear DNA was immunohistochemically stained therewith. The monoclonal anti-single-stranded DNA antibody was prepared as will be described hereinbelow.

A suspension of single-stranded DNA-MBSA, prepared through a process similar to the process as described in Example 1, was emulsified by adding an equal volume of the complete Freund's adjuvant to obtain an emulsion of 50 $\mu$g single-stranded DNA/200 $\mu$l. 200 $\mu$l of the emulsion was injected into the peritoneal cavity of Balb/C mouse (8 weeks-female) as a first priming. The immuno-boosting was carried out by conducting intra-peritoneally injection of the single-stranded DNA-MBSA suspension at a dosage of 100 $\mu$g single-stranded DNA/200 $\mu$l for 2 times at 2 weeks interval.

At the 4th day after the boosting, the immunized mouse was sacrificed and the spleen was taken out, then the spleen cell was fused with murine myeloma cell (SP-2, Sp-2/O -Ag14) through the ordinary process, which was conducted with the use of polyethylene glycol. The clones having the anti-ssDNA activity in the supernatant of the cultured medium were selected through the ELISA method, and then subjected to the limiting dilution-culture method for 3 times to establish the monoclonal cell line.

The thus obtained monoclonal antibody-producing cells were suspended in saline to prepare a suspension of $1 \times 10^7$ cells/ml, and the thus prepared cell suspension was injected intra-peritoneally to a Balb/C mouse (15 weeks; female). The mouse used had been intra-peritoneally administrated with 0.5 ml of Pristane (2,6,10,14-tetramethyl pentadecane; first grade class chemical; produced by WAKO Pure Chemical Industries, Ltd.) for two times at an interval of 7 days; and at the 4th day after the secondary dosage with the Pristane, the monoclonal antibody-producing cell suspension was injected as aforementioned. At the 7th day after the cell injection, the antibody-containing ascites produced in the abdomen of the mouse was collected, and after removing the cell components therefrom by centrifugation, the IgG fraction thereof was collected through the ammonium sulfate precipitation method, followed by further refining of the antibody by the Protein A Sepharose affinity chromatography. Using the thus obtained monoclonal antibody, the immunohistochemical staining was conducted as follows.

At the staining step, the tissue obtained by surgical excision or erasion, the tissue taken by biopsy or the tissue taken by autopsy was fixed by immersing the same in a 10% formalin buffer solution for one to two nights, dehydrated by rinsing with flowing ethanol and further with xylene, respectively, for 24 hours, immersed in paraffin heated to 60° C. for about 2 hours, and then placed on a mold to be embedded in paraffin to prepare a paraffin-embedded block of the tissue. The paraffin-embedded block was sliced using a microtome to prepare tissue sections which were placed on slide glass plates. Each of the tissue sections was immersed in four vessels each containing therein xylene successively for 4 minutes to deparaffinized, then immersed likewise in four vessels each containing ethanol respectively for 4 minutes, and then immersed in a vessel containing PBS to replace ethanol with PBS. Subsequently, a solution (0.1 mg/ml in PBS) of RNase (Ribonuclease A, Type-AS, from bovine pancreas; produced by Sigma, USA) was overlaid on the tissue section on the slide glass plate, followed by incubation in an incubator maintained at 37° C. for 30 minutes to digest RNA, in which the anti-ssDNA antibody was recognizable.

After the completion of the RNase reaction, the slide glass plate was rinsed in a vessel containing PBS for 5 minutes for every three time rinsings. The slide glass plate carrying the tissue section was immersed in a 2N hydrochloric acid solution, which has been preliminarily warmed to 30° C., and then placed in an incubator maintained at 30° C. for 20 minutes to hydrolyze DNA. Immediately after hydrolysis, the slide was rinsed in a vessel containing PBS for 5 minutes for every four time rinsings, and then the slide was mounted with 1% skim milk-PBS for blocking the non-specific binding of antibody. After removing the skim milk-PBS, the anti-single-stranded DNA monoclonal antibody diluted with 0.1% skim milk-PBS by 50 times, was mounted on the slide and allowed to stand for reaction at 4° C. overnight. Immediately after the completion of reaction, the slide glass plate was rinsed in a vessel containing PBS for 5 minutes for every three times; and then the slide glass plate was overlaminated with a biotin-labelled anti-mouse IgG antibody of Immu-Mark Universal Kit (produced by ICN Immuno Biologicals) for a processing time of 2 hours, and then with peroxidase-labelled streptavidin of Immu-Mark Universal Kit (produced by ICN Immuno Biologicals) for a processing time of an hour, and then placed in an incubator maintained at 37° C. for reaction. After the reaction, the slide was rinsed in a vessel containing PBS for 5 minutes for every 3 times, immersed in a vessel containing a DAB-cobalt solution having the composition as set forth below for 5 minutes, and then added with 10 μl of a 3% $H_2O_2$ solution to be colored for 15 to 30 minutes (DAB-cobalt coloring).

Composition of the DAB-Cobalt Solution Used

| | |
|---|---|
| DAB (3,3'-diaminobenzidine tetrahydrochloride dihydrate (produced by WAKO Pure Chemical Industries, Ltd.)) | 50 mg |

-continued

| | |
|---|---|
| 0.05 M Tris-HCl Buffer, pH 7.6 | 100 ml |
| $CoCl_2.6H_2O$ (1% Aqueous Solution; produced by NAKARAI TESQUE, INC. (Cat. No. #09206)) | 2 ml |

The slide was rinsed with flowing water, immersed in the kernechtrot staining solution for 30 seconds, followed by sufficient rinsing with flowing water to put the morphologic tissue structure for easier observation, and subsequently observed through a transmission microscope.

Figure 4:
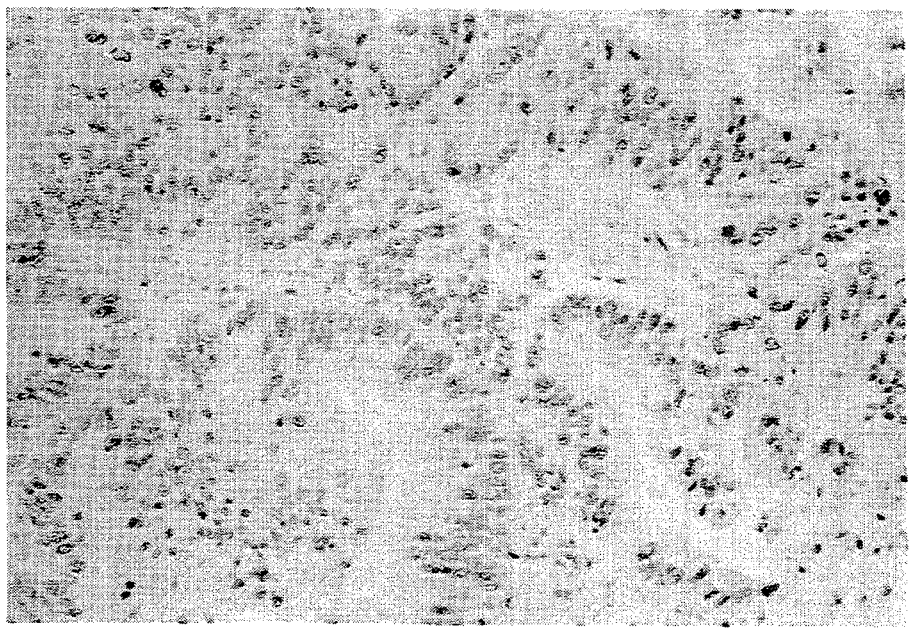

As shown in FIG. 4, at the cancerous portion, nuclear DNA is single-stranded by the treatment with hydrochloric acid to be conjugated with the anti-ssDNA monoclonal antibody, and the conjugation bond between the mouse IgG and avidin through the biotinized anti-mouse IgG antibody was distinctively stained brownish. This figure is a picture of carcinoma of the large intestine, in which cancer cells are densely grown, and it has been observed that only the cancer cell nuclei are stained to liver brown distinctively and selectively.

Figure 5:
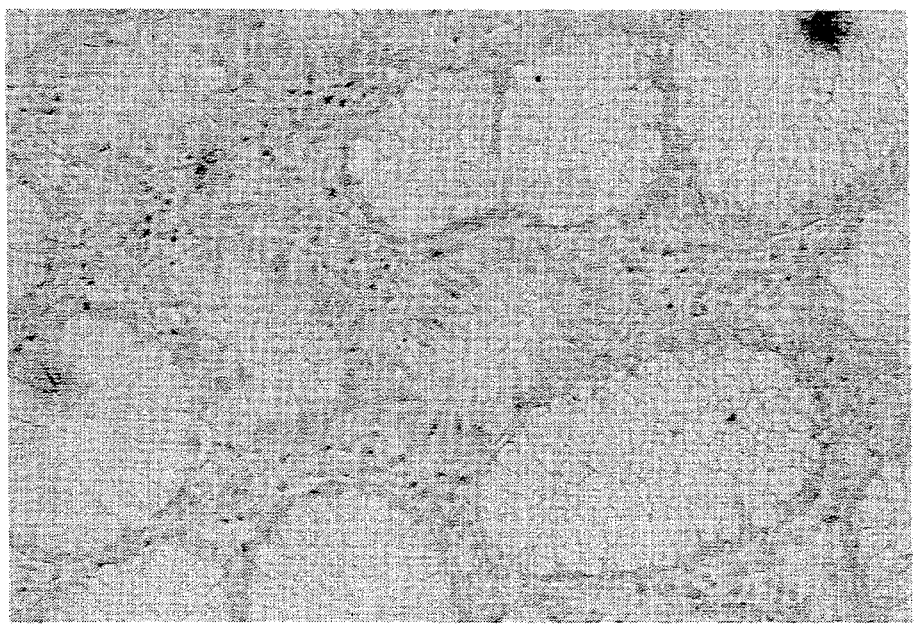

The tissue shown in FIG. 5 is the normal mucosa of the large intestine of the same patient, the tissue being stained under the same condition, and it will be apparent that no cell, which has been stained to liver brown as found in FIG. 4. As should be appreciated from the foregoing, it has been revealed that the staining with an anti-ssDNA monoclonal antibody can be utilized as the means for the discrimination of normal cells from cancer cells.

What is claimed is:

1. A method for detecting the presence of injured nuclear DNA in a pathological tissue specimen comprising the steps of:
   (A) treating a pathological tissue specimen with an acid to selectively hydrolyze only injured DNA in said pathological tissue specimen and to form single-stranded DNA,
   (B) treating the resulting pathological tissue specimen of step (A) with an anti-single-stranded DNA antibody which does not specifically bind double-stranded DNA, and
   (C) subjecting the resulting pathological tissue specimen of step (B) to morphological inspection to detect the presence of binding of said single-stranded DNA with said antibody, wherein the binding of said antibody to said single-stranded DNA indicates the presence of injured nuclear DNA in a pathological tissue specimen.

2. The method according to claim 1, wherein said acid is an inorganic acid.

3. The method according to claim 1, wherein step (A) is effected by adding a dilute acid solution to said pathological tissue specimen, followed by hydrolysis at a temperature of not higher than 40° C. for 5 to 120 minutes.

4. The method according to claim 3, wherein step (A) is effected by adding a dilute acid solution to said pathological tissue specimen, followed by hydrolysis at a temperature of from 20° to 35° C. for 15 to 30 minutes.

5. The method according to claim 1, wherein said anti-single-stranded DNA antibody is labelled with a pigment.

6. The method according to claim 5, wherein said pigment is a colored dye.

7. The method according to claim 5, wherein said pigment is a fluorescent dye.

8. The method according to claim 1, wherein said anti-single-stranded antibody is labelled with an enzyme or a coenzyme, and the presence of binding in step (C) is detected by reaction of said enzyme or coenzyme with a coloring substance.

9. The method according to claim 1, wherein said anti-single-stranded DNA antibody is anti-serum obtained from an animal immunized with said single-stranded DNA.

10. The method according to claim 1, wherein said anti-single-stranded DNA antibody is a monoclonal antibody.

11. The method according to claim 1, wherein in step (C) said pathological tissue specimen is stained by immuno-histochemical staining using second antibody which binds to said anti-single-stranded DNA antibody, and the thus stained tissue is inspected to detect the presence of binding of said single-stranded DNA to said anti-single-stranded DNA antibody.

12. The method according to claim 1, wherein said pathological tissue specimen is treated with RNase prior to said treatment with said acid.

13. The method according to claim 1, wherein said pathological tissue specimen is subjected to counternuclear staining after it is treated with said anti-single-stranded DNA antibody.

* * * * *

UNITED STATES PATENT AND TRADEMARK OFFICE
CERTIFICATE OF CORRECTION

PATENT NO. : 5,369,002

DATED : November 29, 1994

INVENTOR(S) : MASARU FUKUDA

It is certified that error appears in the above-indentified patent and that said Letters Patent is hereby corrected as shown below:

In column 2, line 10, delete "to".

In column 2, line 54, delete "mode thereof".

Signed and Sealed this

Second Day of May, 1995

Attest:

BRUCE LEHMAN

Attesting Officer     Commissioner of Patents and Trademarks